United States Patent [19]

Kraft et al.

[11] 3,975,156

[45] Aug. 17, 1976

[54] METHOD AND MATERIAL FOR DETECTING AND QUANTITATING FETAL ERYTHROCYTES IN ADULTS

[75] Inventors: Patricia J. Kraft, Somerville; Marcia R. Thomas, Neshanic Station; Larry A. Kraft, Somerville, all of N.J.

[73] Assignee: Ortho Diagnostics, Inc., Raritan, N.J.

[22] Filed: Nov. 10, 1975

[21] Appl. No.: 630,597

[52] U.S. Cl. .............................. 23/230 B; 424/11; 252/408
[51] Int. Cl.[2] .......................................... G01N 33/16
[58] Field of Search ................. 23/230 B; 252/408; 424/3, 7, 11; 260/537 R

[56] References Cited
UNITED STATES PATENTS

| 2,761,808 | 9/1956 | Singher et al. ........................ 424/11 |
| 3,873,272 | 3/1975 | Wakefield et al. .................. 424/7 X |
| 3,925,020 | 12/1975 | Ogawa et al. ..................... 23/230 B |

OTHER PUBLICATIONS

*Gradwohl's Clinical Laboratory Methods and Diagnosis,* 7th Ed., vol. 1, Mosby Co., St. Louis (1970), pp. 784–785.

*Primary Examiner*—Morris O. Wolk
*Assistant Examiner*—Timothy W. Hagan

[57] ABSTRACT

By differential elution of hemoglobin from fetal and adult erythrocytes using a succinic acid/succinate or a malic acid/malate buffer, fetal erythrocytes in adult blood may be detected and quantitated.

15 Claims, No Drawings

METHOD AND MATERIAL FOR DETECTING AND QUANTITATING FETAL ERYTHROCYTES IN ADULTS

BACKGROUND OF THE INVENTION

The present invention relates to the detection and quantitation of fetal erythrocytes in adult blood and more particularly to the detection and quantitation of fetal-maternal hemorrhages wherein the mother is Rho(D)-negative and the fetus is Rho(D)-positive.

The detection and quantitation of fetal erythrocytes in adult blood is important in diagnosis of numerous maladies, such as for example, sickle-cell anemia and other hereditary blood disorders. It is also important in the detection of ante-natal placental transfer and fetal-maternal hemorrhage in pregnant women. While the method of the invention is applicable to the detection and quantitation of fetal erythrocytes in adult blood for whatever reason, this latter purpose will be used as an illustration throughout this application.

When there is incompatibility between the blood of a fetus and the blood of the mother, an immunization reaction can occur if there is transfer of fetal blood into the maternal blood stream. Such transfer can occur either through ante-natal placental transfer or through fetal-maternal hemorrhage (FMH) at childbirth, in the process of a spontaneous or induced abortion, or because of obstetric trauma. This immunization has an extremely adverse affect on the ability of the mother to carry a subsequent fetus having the same incompatibility, because the immune reaction built up by the blood of first child may cause spontaneous abortion of the subsequent fetus, hemolytic disease of the newborn, or other disorders. It is therefore desirable in the case of incompatibility, and especially in the case of Rh-incompatibility, to inject the appropriate antibody into the mother just after such transfer has occured in order to react with the fetal antigen and thus prevent the immune reaction from developing.

It is known that approximately 20 micrograms of anti-Rho(D) antibody will suppress the antigenic effect of one ml of packed erythrocytes. It is therefore the procedure at present to administer a dose of approximately 300 micrograms of Rho(D) immune globulin (human) (e.g. RhoGAM globulin manufactured by Ortho Diagnostics, Inc.) to an Rho(D)-negative mother within 72 hours after the delivery of an Rho(D)-positive child, which delivery may involve an FMH. While this dose of RhoGAM globulin is sufficient for neutralizing FMH in the majority of cases, some types of FMH are not neutralized by this dose, probably because of a so-called "massive" hemorrhage (one transferring more than about 15 ml of packed erythrocytes). Further, in the case of ante-natal placental transfer, it is important to monitor the quantities of erythrocytes being transferred. It is therefore necessary for satisfactory treatment of fetal erythrocyte transfer to have a test for determining the extent of said transfer so that the dosage of RhoGAM globulin or other treating agent may be adjusted accordingly.

It is known that fetal hemaglobin is less readily eluted from the fetal erythrocyte than is adult hemoglobin from the adult erythrocyte at a pH of about 3.2–3.3. This fact has been utilized in designing prior art methods to determine the extent of fetal-maternal hemorrhage. In such prior art tests the pH of 3.2–3.3 has been deemed critical to produce optimum differential elution of adult erythrocytes relative to fetal erythrocytes.

The following steps are an outline of prior art methods for detecting fetal erythrocytes in adult blood by differential elution:

A. A smear of blood is prepared on a slide and is dried;
B. The smear is fixed on the slide, for example, by treatment with a loweralkanol, and again air dried;
C. The fixed slide is immersed in an elution buffer to differentially elute the adult erythrocytes relative to the fetal erythrocytes;
D. The eluted smear is stained; and
E. The presence of fetal erythrocytes and number of fetal erythrocytes and adult erythrocytes are determined.

The prior art test which has received the widest clinical acceptance is the so called Kleihauer-Betke test and modifications thereof. In this prior art test, a thin smear of maternal blood which has been treated with an anticoagulent is fixed onto a slide in 80 percent aqueous ethanol. The smear is then eluted in a citric-phosphate buffer at pH 3.3 for five minutes at 37° to cause differential elution of adult erythrocytes relative to fetal erythrocytes, after which the smear is stained with hematoxylin and erythrosin to stain the hemoglobin-containing fetal erythrocytes. Inspection of the slide under a microscope reveals the stained fetal erythrocytes and the colorless, transparent so-called "ghost" eluted adult erythrocytes. In the Kleihauer test and its modifications, the "ghost" erythrocytes are difficult to count both because of their colorless transparency and also because some of the adult erythrocytes are often fragmented during the elution process. There are many variations of this test, but they are all referred to as "Kleihauer tests."

The Kleihauer-Betke test, however, suffers several disadvantages. First, the reagents must be freshly prepared at the time the test is conducted; they are generally not stable for longer than 24 hours. Second, the test takes over an hour to set up and run, excluding the time for the preparation of the reagents. Third, the results are sufficiently variable and sufficiently difficult to interpret that the test is not believed to be truly quantitative. That is, while it is possible using the Kleihauer test to determine the presence of a massive fetal-maternal hemorrhage, it is not always possible to determine the extent of such hemorrhage due to the difficulty in counting the barely-visible "ghost" erythrocytes discussed above.

The method of the present invention obviates these disadvantages of the prior art. It is both rapid and convenient. Moreover, the present method allows ready quantitation of the amount of fetal erythrocytes both because of the visibility of the eluted adult erythrocytes and because there is no fragmentation of adult erythrocytes during the elution. The reagents used therein are stable for long periods of time and may conveniently be stored until needed. Further, these reagents may easily be mass produced.

SUMMARY OF THE INVENTION

There is provided by the present invention a method and materials for detecting and quantitating fetal erythrocytes in adult blood and a method for preparing such materials.

The method of the invention differs from that of the prior art primarily in that a novel buffer is used. The novel buffer of the invention comprises an aqueous solution of malic acid and a malate salt or an aqueous solution of succinic acid and a succinate salt. By use of this buffer in place of prior art buffers for differential elution of adult erythrocytes relative to fetal erythrocytes, better detection and quantitation of fetal erythrocytes is obtained. This buffer may be conveniently dried for storage prior to use, and is indefinitely stable in this dry state.

The eluting buffer of the invention comprises an aqueous solution of an acid of formula:

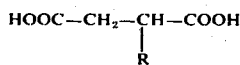

weight less
wherein R is a member selected from the group consisting of hydrogen and hydroxy, and salts thereof. The cation of these salts is at least one member selected from the group consisting of alkali metal ions of atomic weightless than 133 and alkaline earth metal ions of atomic weight less than 138. The cation is preferably an alkali metal ion and more preferably sodium ion. A preferred buffer of the invention consists essentially of an aqueous solution of the above acid and salt.

If the buffer is succinic acid/succinate (R=H), it is preferred that the pH thereof be between about 3.73 and 3.83 and that the total succinate concentration be about 0.001 M. The succinic acid/succinate buffer is less preferred because it is less stable in a liquid state than is the malic acid/malate buffer.

The preferred buffer of the invention is malic acid/malate (R=OH) having a pH between about 4.05 and 4.25, more preferably about 4.13. With this preferred buffer, an elution time of from about 15 to about 25 seconds at about 36°–38°C causes optimum differential elution. It should be understood that the temperature and time of elution may be varied within wide ranges for a particular pH and still be within the scope of the present invention, so long as differential elution of the fetal and adult erythrocytes is obtained.

In light of the prior art teaching that the pH of an eluting buffer should be in the range 3.2–3.3 in order to achieve optimum differential elution, it is a surprising feature of the present invention that a succinic acid/succinate buffer of about pH 3.78 and a malic acid/malate buffer of about pH 4.13 also cause optimum differential elution. The effectiveness of the malic acid/malate buffer is particularly surprising because it would be a poor buffer at pH 3.2–3.3. The buffers of the invention are more effective in causing differential elution than those of the prior art because the eluted adult erythrocytes are readily visible and are intact (not fragmented).

There are also included within the scope of the present invention the method of preparing the eluting buffer used in the above method and the eluting buffer itself.

For some purposes, it is preferred to convert the eluting buffer of the invention to a dry state and then reconstitute the material by addition of water prior to use. This procedure causes the eluting buffer of the invention to be indefinitely stable (in its dry state) without the necessity of adding any bacteriostatic agents or the like. Bacteriostatic agents may, however, be added to the buffer to prevent bacterial growth during manufacture.

The succinic acid/succinate buffer of the invention may be prepared by combining appropriate amounts of succinic acid and a succinate salt (e.g., sodium succinate), diluting the resulting mixture with a sucrose filler, and dispensing an appropriate amount of the dry filled buffer into a vial. The buffer may be prepared for use by the addition of water as illustrated in the examples below.

To prepare the preferred malic acid/malate elution buffer of the invention, one may titrate a solution of malic acid with aqueous sodium hydroxide to attain the optimum pH for the elution process. The total malate concentration in this dilute buffer should be from about 0.001M to about 0.1M and preferably from 0.015M to 0.025M. The expressions "total malate concentration" and "total succinate concentrations" as used herein means the total concentration of malic acid and malate ion (or succinic acid and succinate ion) in the buffer solution. The buffer is preferably evaporated to dryness before use for some purposes and then reconstituted by addition of water. It is desirable that a concentrated buffer be prepared in this instance to facilitate the drying.

However, it was surprisingly discovered that when the dried buffer was reconstituted by addition of water to produce the dilute buffer, the pH of this dilute buffer varied randomly from the calculated value based on the pH of the concentrated buffer. Thus, for example, the pH of a dilute buffer about 0.02M in total malate should be about 4.13 if the pH of the concentrated buffer about 0.8M in total malate is 3.83. But reconstitution of dried buffer made from this concentrated buffer yielded dilute buffers having pH values generally lower than 4.13. This variation of more than 0.01 pH units from the calculated value on reconstitution of the solid dried buffer is called "pH shift." It is believed that this pH shift would also occur after reconstitution of a dried buffer prepared from the dilute buffer.

It was then discovered that by autoclaving the concentrated solution of malic acid prior to titration, there was no undesirable pH shift on later reconstitution of the dried buffer. The particular autoclaving conditions which were used were about 120°C and about 15 pounds per square inch for about 1 hour, but it should be understood that any autoclaving or heating sufficient to prevent a pH shift in the reconstituted dilute buffer is included within the scope of the present invention. Without the autoclaving or heating taught above, the pH of the resulting dilute buffer may vary from the calculated value, which is highly undesirable.

The concentrated malic acid solution is preferably titrated to a pH from about 3.76 to about 3.90 so that the resulting dilute buffer prepared by reconstitution of the solid dried buffer will have a pH from about 4.05 to about 4.25.

The concentrated buffer, the dilute buffer, and the dried buffer are all included within the scope of the present invention.

In the test method of the invention, the smear is preferably fixed on the slide by immersing the slide in an aqueous solution of a loweralkanol. The preferred fixing solution may be methanol, ethanol, isopropanol, or the like loweralkanol. A more preferred fixing solution is 70 to 90 volume percent aqueous methanol and most preferably 82 to 85 volume percent aqueous methanol. The slide is immersed in the alkanol for a time sufficient to cause fixing of the erythrocytes to the slide in such a manner as to promote optimum differential elution in the elution step.

The fixed slide is then immersed in the eluting buffer of the invention as described above for a time sufficient to cause optimum differential elution. The differential elution caused is dependent upon the pH of the buffer, the temperature of the eluting solution, and the time for which the slide is immersed therein, as well as on the identity of the fixing solution and the time of fixing.

A preferred method of preparation of the concentrated and dried elution buffer of the present invention is illustrated by the following Example.

EXAMPLE I

A 0.8M aqueous solution of malic acid was prepared by dissolving 90 mg of thimerosal (bacteriostatic agent) in 900 ml of purified water (Solution A) and then dissolving 107.27g of malic acid in 300 ml of Solution A with warming to 27 ± 5°C. The resulting malic acid solution was autoclaved for 60 minutes at 122 ±1°C at 15 p.s.i. pressure and then cooled to 27 ±5°C. The resulting autoclaved malic acid solution was then titrated to a pH of 3.83 ± 0.01 with 6.0M sodium hydroxide. The resulting solution was then diluted to 1000 ml with Solution A and mixed thoroughly to produce the concentrated buffer.

The concentrated buffer was then dispersed into vials (1.00 ml/vial), and the filled vials were dried in a low temperature oven (below 65°C) until the residual water was not more than 15.4 micro g/mg of dried buffer. The vials were capped and stored until used.

A preferred embodiment of the test method of the present invention is illustrated by the following example.

EXAMPLE II

A vial of dried elution buffer as prepared in Example I was opened and 40 ml of distilled water was added thereto to produce a buffer of pH about 4.13 which is about 0.02M in total malate concentration. The vial was capped and placed in a 37°C water bath. A second vial containing erythrosin B dye was opened and 40 ml of distilled water was added thereto. The vial was capped, shaken to mix and left at room temperature. A third vial of fixing solution, which comprises about 84% by weight aqueous methanol, was left at room temperature.

Into a clean test tube were placed four drops of isotonic saline solution and two drops of blood containing 1.5 mg EDTA per 1 ml whole blood, and the whole was mixed by shaking gently. A thin smear of this diluted blood was prepared using a clean glass slide, after which the slide was thoroughly air dried. The dried glass slide was placed in the vial of fixing solution for 6 minutes at room temperature, after which it was rinsed thoroughly in a beaker of fresh distilled water and air dried. The capped vial of elution buffer was inverted several times to assure a uniform temperature throughout and was then uncapped and replaced in the 37°C water bath. The slide was immersed in the eluting buffer with gentle agitation for exactly 20 seconds, after which it was immediately transferred to the dye solution, where it was allowed to remain for about 1 minute. The slide was then thoroughly rinsed in a beaker of fresh distilled water and thoroughly air dried.

The eluted stained slide was read within 24 hours of staining to obtain maximum stain contrast, although the slide may be stable for a longer period. Under magnification at 250×, the uneluted fetal cells appear bright red in contrast to the pale pink eluted adult cells. Eight randomly selected fields were counted to obtain a representative ratio of fetal erythrocytes per thousand adult erythrocytes.

The ratio of fetal erythrocytes to adult erythrocytes observed is linearly related to the ratio of these materials in the total blood volume. From this latter ratio, the amount of RhoGAM globulin (or any other antibody) which should be administered can be determined.

The foregoing examples have been given by way of illustration only and not to limit the scope of the present invention, which scope is defined in the appended claims.

What is claimed is:

1. In a method of measuring the number of fetal erythrocytes relative to adult erythrocytes in adult blood which has the steps of: (A) preparing a smear of said blood on a glass slide; (B) fixing said smear on said slide; (C) differentially eluting said adult erythrocytes of said smear relative to said fetal erythrocytes with an eluting buffer; (D) staining said slide with a protein-staining material; and (E) measuring the number of stained fetal erythrocytes and adult erythrocytes on at least a portion of the slide;

The improvement wherein the eluting buffer comprises an aqueous solution of an acid of formula:

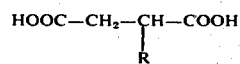

wherein R is a member selected from the group consisting of hydrogen and hydroxy, and a salt thereof wherein the cation of said salt is a member selected from the group consisting of alkali metal ions of atomic weight less than 133 and alkaline earth metal ions of atomic weight less than 138.

2. The method of claim 1 wherein the buffer is a succinic acid/succinate buffer.

3. The method of claim 1 wherein the buffer is a malic acid/malate buffer.

4. The method of claim 3 wherein the total malate concentration of the buffer is from about 0.001M to about 0.1M.

5. The method of claim 4 wherein the buffer has a pH of from about 4.05 to about 4.25.

6. The method of claim 5 wherein said buffer has a total malate concentration of from about 0.15 to about 0.025M, the temperature of said buffer is from about 36°C to about 38°C, and said smear is immersed in said buffer for about 15 to about 25 seconds.

7. The method of claim 3 wherein fixing the smear is accomplished by immersing said slide in an aqueous loweralkanol.

8. The method of claim 7 wherein the aqueous loweralkanol is aqueous methanol having a concentration of from about 82 to about 85 percent by volume.

9. A method for preparing a concentrated malic acid/malate buffer which is conveniently evaporated to produce an indefinitely stable, solid buffer material, which material may be reconstituted by addition of water to a buffer having a known pH and no pH shift; which method comprises the steps of:

A. preparing a concentrated aqueous solution of malic acid;

B. heating said malic acid solution at a temperature and for a time sufficient such that no pH shift occurs on reconstitution of the solid buffer material with water; and C. titrating this heated malic acid solution with a concentrated aqueous alkali metal hydroxide solution to a desired pH to yield a concentrated buffer solution.

10. The method of claim 9 wherein the malic acid solution in step A has a concentration of from about 0.8 to about 1.6 molar.

11. The method of claim 9 wherein the malic acid solution is heated at greater than 100°C for at least about 1 hour.

12. The method of claim 8 wherein the desired pH of the concentrated buffer solution is from about 3.76 to about 3.90.

13. The method of claim 8 which further comprises evaporating a portion of said concentrated buffer solution to obtain an indefinitely stable dried buffer composition from which a dilute buffer can be prepared by addition of water, which dilute buffer has no pH shift.

14. A dried buffer composition as prepared by the method of claim 12.

15. A buffer for use in detecting and quantitating fetal erythrocytes in adult blood which consists essentially of malic acid, an alkali metal malate salt, and water, and which has a pH from about 4.05 to about 4.25 and a total malate concentration of from about 0.015 to about 0.025M.

* * * * *

UNITED STATES PATENT AND TRADEMARK OFFICE
CERTIFICATE OF CORRECTION

PATENT NO. : 3,975,156
DATED : August 17, 1976
INVENTOR(S) : Kraft, Patricia J. et al It is certified that error appears in the above-identified patent and that said Letters Patent are hereby corrected as shown below:

In Column 3, Line 16, "weight less" should not be there ---.

In Column 3, Line 21, "weightless" should read --- weight less ---.

In Column 6, Claim 6, Line 49, "0.15" should read --- 0.015 ---.

Signed and Sealed this twelfth Day of July 1977

[SEAL]

Attest:

RUTH C. MASON
*Attesting Officer*

C. MARSHALL DANN
*Commissioner of Patents and Trademarks*